United States Patent [19]

Priddy

[11] 3,947,418

[45] Mar. 30, 1976

[54] HETEROCYCLIC PEROXIDES

[75] Inventor: Duane B. Priddy, Midland, Mich.

[73] Assignee: The Dow Chemical Company, Midland, Mich.

[22] Filed: Oct. 4, 1974

[21] Appl. No.: 512,283

Related U.S. Application Data

[62] Division of Ser. No. 385,914, Aug. 6, 1973, Pat. No. 3,890,316.

[52] U.S. Cl....... 260/246 B; 260/293.64; 260/326.8
[51] Int. Cl.² .................................... C07D 295/10
[58] Field of Search ........ 260/246 B, 293.64, 326.8

[56] References Cited
OTHER PUBLICATIONS
Batog et al., C. A., 72:31170w, (1970).
Lederer, Chem. Ber., 105, pp. 55:19956f,
Rieche et al., C. A., 55:19956f, (1960).

Primary Examiner—Lorraine A. Weinberger
Assistant Examiner—Michael Shippen
Attorney, Agent, or Firm—Glwynn R. Baker

[57] ABSTRACT

Heterocyclic nitrogen-containing peroxides are prepared by reacting a tertiary alkyl hydroperoxide with a nitrogen heterocycle substituted by cycloalkene such as 1-(4-morpholinyl)cyclohexene. The products are useful initiators of vinyl polymerization where a peroxide initiator of relatively high thermal stability is desirable.

1 Claim, No Drawings

HETEROCYCLIC PEROXIDES

CROSS REFERENCE TO RELATED APPLICATION

This application is a divisional of my application Ser. No. 385,914 filed Aug. 6, 1973, now U.S. Pat. No. 3,890,316, granted June 17, 1975.

BACKGROUND OF THE INVENTION

This invention relates to new chemical compounds and it relates particularly to new heterocyclic nitrogen containing organic peroxides having enhanced thermal stability.

Peroxides containing heterocyclic nitrogen substituents have been made before and are known to be capable of initiating vinyl polymerization. Compounds of the classes represented by 4-morpholinylmethyl α,α-dimethyl-benzyl peroxide and bis(1-(1-piperidinyl)cyclopentyl) peroxide are disclosed by Rieche et al., Chem. Ber. 92, 1206–9 (1959), see also German Pat. No. 1,098,513. These compounds are capable of initiating the polymerization of styrene, for example, upon heating. However, the relatively low decomposition temperature of these peroxides limits their utility in this application.

SUMMARY OF THE INVENTION

It has now been found that considerably greater thermal stability and consequently broader utility in vinyl polymerization processes are obtained in nitrogen heterocyclic substituted peroxides having one of the formulas:

(I) $(R' - O - O - R)_n Y$ wherein
R is a cycloalkylidene radical of 5–7 carbon atoms,
R' is α,α-dimethylbenzyl, lower alkyl-α,α-dimethylbenzyl, or a tertiary alkyl group of 4–8 carbon atoms,
Y is a nitrogen-bonded heterocyclic radical of the group
 4-morpholinyl,
 1-piperidinyl,
 1-pyrrolidinyl,
 1,4-piperazinediyl, and the lower alkyl derivatives thereof, and n is the valence of Y, i.e., 1 or 2.

(II) $R''+O-O-R-4')_2$ wherein
R'' is one of the divalent radicals 1,1,4,4-tetra-methyltetramethylene and phenylenediisopropylidene.
R is as previously defined, and
Y' is one of the monovalent heterocyclic radicals
 4-morpholinyl,
 1-piperidinyl, and
 1-pyrrolidinyl.

These compounds are easily prepared by reacting an appropriate hydroperoxide with an olefinic compound under moderate conditions whereby a simple addition reaction takes place. Most conveniently, the hydroperoxide R'OOH is reacted with the substituted cycloolefin represented by $YA_n$ or Y'A wherein A is a 1-cycloalkenyl radical.

DETAILED DESCRIPTION

The family of compounds of this invention can be classified into two principal groups, those where the heterocyclic radical Y is monovalent and those where it is the divalent 1,4-piperazinediyl radical. The first group is composed of monoperoxides with the general formula

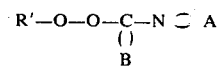

and diperoxides with the general formula

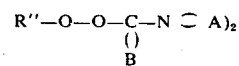

where A is an alkylene or oxydialkylene radical of 4 to about 10 carbon atoms and B is an alkylene radical of 4–6 carbon atoms. The second group, of course, is the corresponding diperoxide with the peroxycycloalkyl substituent on each nitrogen atom of the piperazine molecule. These compounds have the general formula

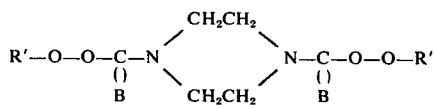

where R' and B have the values previously defined.

As noted above, all the above compounds are preferably prepared by reacting the hydroperoxide R'OOH or HOOR''OOH with the appropriate cycloolefinic compound. The reaction is normally accomplished by merely mixing the hydroperoxide, preferably in excess, with the olefin at ambient temperature, preferably in an inert solvent reaction medium such as ether or low boiling aliphatic hydrocarbon from which the product is conveniently isolated by filtration or by evaporating the solvent and excess hydroperoxide. The peroxide products are white crystalline solids melting without decomposition at low to moderate temperatures.

Typical hydroperoxides useful in the above method for making the new compounds include tert-butyl hydroperoxide, tert-amyl hydroperoxide, 1,1-dimethylbutyl hydroperoxide, 1,1,3,3-tetramethylbutyl hydroperoxide, p,α,α-trimethylbenzyl hydroperoxide, cumene hydroperoxide, α-ethyl-α-methylbenzyl hydroperoxide, p-tert-butyl-α,α-dimethylbenzyl hydroperoxide, and 1,1,2,2-tetramethylpropyl hydroperoxide.

Dihydroperoxides useful for making compounds of formula II are 1,1,4,4-tetramethyltetramethylenedihydroperoxide and phenylenediisopropylidene dihydroperoxide.

N-Cycloalkenyl heterocycles which are suitable coreactants include
4-(1-cyclohexenyl)morpholine,
1-(1-cyclopentenyl)piperidine,
1-(1-cycloheptenyl)pyrrolidine,
4-(3-methyl-1-cyclopentenyl)morpholine,
1,4-bis(1-cyclohexenyl)-2,5-diethylpiperazine,
1-(4-methyl-1-cyclohexenyl)-2-isopropylpyrrolidine,
1-(1-cyclopentenyl)-3-methylmorpholine,
1,4-bis(1-cyclohexenyl)piperazine, and
1-(1-cyclohhexenyl)-3-ethylpiperidine.

These reactants are readily prepared from the nitrogen heterocycle and the appropriate cycloalkanone by conventional procedures.

Theoretically, a polymeric polyperoxide would be produced by reacting a dihydroperoxide such as defined here with a 1,4-bis(1-cycloalkenyl)piperazine. However, the product actually obtained from this reaction is a gummy, resinous material of poor solubility which, although it contains some peroxide groups, has little practical utility.

Example 1

A solution of 4.5 g. of tert-butyl hydroperoxide in 30 ml. of ether was made up and 1.67 g. of 4-(1-cyclohexenyl)morpholine was added at room temperature. The reaction mixture was stirred for one hour and then was washed with cold 2% aqueous NaOH. The organic layer was dried over anhydrous sodium sulfate and the ether was evaporated to leave a residue of 2 g. of white crystalline solid, m.p. 43°–46°C. This was identified as tert-butyl 1-(4-morpholinyl)cyclohexyl peroxide with the structure

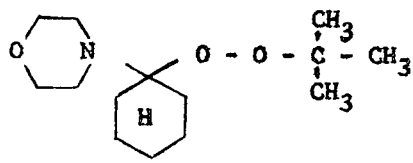

Identification was by warming a sample in aqueous sodium iodide and titrating the liberated iodine with standard thiosulfate solution.

Example 2

A quantity of 1,4-bis(1-cyclohexenyl)piperazine was added to a solution of 20 g. of cumene hydroperoxide in 100 ml. of ether at room temperature. A white precipitate formed after stirring for 30 seconds. After another 15 minutes, the reaction mixture was filtered to obtain 5.5 g. of a white solid, m.p. 104°–105°C. This was identified as before as (1,4-piperazinediyldicyclohexylidene) bis (α,α-dimethylbenzyl peroxide) having the structure

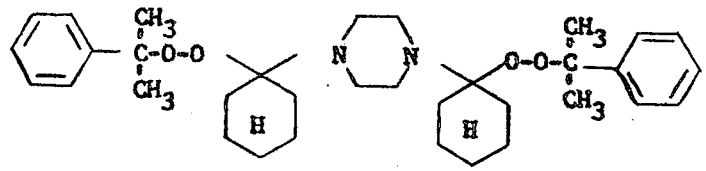

Example 3

The procedure of Example 2 was repeated using 10 g. of tert-butyl hydroperoxide in 75 ml. of ether as the peroxide reactant. The product was 3.5 g. of white solid, m.p. 102°–104°C. This was identified as before as the expected (1,4-piperazinediyldicyclohexylidene)bis-(tert-butyl peroxide) which has the structure

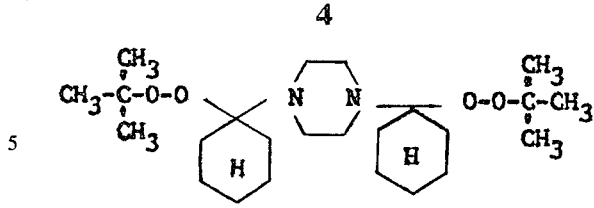

Example 4

A solution of 13 g. of 70% aqueous 1,1,4,4-tetramethyltetramethylene dihydroperoxide in 100 ml. of ether was dried over anhydrous sodium sulfate. The dry ethereal solution was then combined with 16.8 g. of 4-(1-cyclohexenyl)morpholine and the mixture was stirred at 10°–20°C. for 30 minutes. At this point, 200 ml. of cold 5% aqueous NaOH was added and stirring was continued for another five minutes. The ether layer was separated, dried as before, and the ether evaporated to obtain 21 g. of white solid. This was identified as 1,1,4,4-tetramethyltetramethylenebis(1-(4-morpholinyl) cyclohexyl) diperoxide having the structure

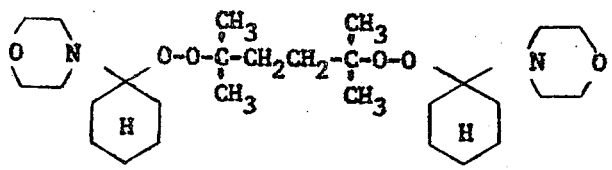

Following the general procedure of the above examples, tert-amyl hydroperoxide is reacted with 1-(1-cyclopentenyl)piperidine to make tert-amyl 1-(1-piperidinyl)cyclopentyl peroxide, 1,1-dimethylpentyl hydroperoxide is reacted with 1-(1-cycloheptenyl)pyrrolidine to make 1,1-dimethylpentyl 1-(1-pyrrolidinyl)-cycloheptyl peroxide, 1,1,3,3-tetramethylbutyl hydroperoxide is reacted with 4-(3-methyl-1-cyclopentenyl)-morpholine to produce 1,1,3,3-tetramethylbutyl 3-methyl-1-(4-morpholinyl)cyclopentyl peroxide, and p-tert-butyl-α,α-dimethylbenzyl hydroperoxide is reacted with 1,4-bis(1-cyclopentenyl)piperazine to make (1,4-piperazinediyldicyclopentylidene) bis(p-tert-butyl-α,α-dimethylbenzyl peroxide). Similarly, p,α,α-trimethylbenzyl hydroperoxide is reacted with 4-(1-cyclohexenyl)morpholine to make p,α,α-trimethylbenzyl 1-(4-morpholinyl)cyclohexyl peroxide, α-ethyl-α-methylbenzyl hydroperoxide is reacted with 1-(1-cyclopentenyl)pyrrolidine to make α-ethyl-α-methylbenzyl 1-(1-pyrrolidinylcyclopentyl peroxide), and 1,1-dimethylhexyl hydroperoxide is reacted with 1,4-bis(3-methyl-1-cyclohexenyl)piperazine to make 1,4-piperazinediylbis(3-methylcyclohexylidene)bis(1,1-dimethylhexyl peroxide).

In the same way, 1,1,4,4-tetramethyltetramethylene dihydroperoxide is reacted with 1-(1-cyclohexenyl)-piperidine to make 1,1,4,4-tetramethyl-tetramethylenebis(1-(1-piperidinyl)cyclohexyl diperoxide and phenylenediisopropylidene dihydroperoxide is reacted with 1(1-cyclopentenyl)pyrrolidine or with 4(1-cyclohexenyl)morpholine to make respectively phenylenediisopropylidenebis(1-(1-pyrrolidinyl)cyclopentyl) diperoxide or phenylenediisopropylidenebis(1-

(4-morpholinyl)cyclohexyl) diperoxide. These examples are similar in appearance and have properties similar to those of the products of Examples 1–4.

Example 5

A solution of 0.103 g. of the product of Example 3 in 50 g. of styrene was prepared and about 5 ml. portions of this solution were sealed in glass ampules for polymerization tests. The filled ampules were heated at 111°C. and the contents of each were analyzed for solids content at different times to follow the progress of the polymerization. The molecular weight and molecular weight distribution were determined for the last sample of polystyrene.

| Sample | Time, Hrs. | % Solids | $M_w$* | $M_n$** | $M_w/M_n$ |
|---|---|---|---|---|---|
| A | 1 | 19.03 | — | — | — |

-continued

| Sample | Time, Hrs. | % Solids | $M_w$* | $M_n$** | $M_w/M_n$ |
|---|---|---|---|---|---|
| B | 2 | 32.34 | — | — | — |
| C | 3.17 | 43.76 | — | — | — |
| D | 3.63 | 48.80 | 230,713 | 103,533 | 2.23 |

*$M_w$ is a weight average molecular weight.
**$M_n$ is a number average molecular weight.
The ratio $M_w/M_n$ is a measure of the width of the molecular weight distribution curve.

I claim:
1. A compound of the formula

R''+O—O—R—y')<sub>2</sub>

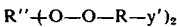

wherein R'' is phenylene diisopropylidene,
R is a cycloalkylidene radical of 5–7 carbon atoms,
Y' is a monovalent heterocyclic radical of the group
4-morpholinyl,
1-piperdinyl, and
1-pyrrolidinyl.

* * * * *

UNITED STATES PATENT AND TRADEMARK OFFICE
CERTIFICATE OF CORRECTION

PATENT NO. : 3,947,418
DATED : March 30, 1976
INVENTOR(S) : Duane B. Priddy

It is certified that error appears in the above-identified patent and that said Letters Patent are hereby corrected as shown below:

Section [56], References Cited, OTHER PUBLICATIONS, delete "Lederer, Chem. Ber., 105, pp. 55:19956f" and insert -- Lederer, Chem. Ber., 105, pp. 2169-74(1972) --

Col. 1, line 48, in the formula, delete the numeral " 4' " and insert -- y' --

Col. 1, line 52, delete the period "." and insert a comma -- , --

Col. 2, line 11, after " R" " and before "O" delete " - " and insert -- ( --

Col. 2, line 65, delete in the parentheses " (1-cyclohhexenyl)" and insert -- (1-cyclohexenyl) --

Col. 4, line 67, insert a hyphen between the "1(" and the "4(", i.e., -- 1-( --   and   -- 4-( --

Col. 6, in Claim 1 the " y' " in the formula should read -- Y' --

Signed and Sealed this

Twenty-eighth Day of September 1976

[SEAL]

Attest:

RUTH C. MASON
*Attesting Officer*

C. MARSHALL DANN
*Commissioner of Patents and Trademarks*